United States Patent
Thompson et al.

(10) Patent No.: US 11,207,023 B2
(45) Date of Patent: Dec. 28, 2021

(54) STIMULUS AND EYE TRACKING SYSTEM

(71) Applicant: Auckland UniServices Limited, Auckland (NZ)

(72) Inventors: Ben Thompson, Auckland (NZ); Jason Te Wharekotua Turuwhenua, Auckland (NZ)

(73) Assignee: Auckland UniServices Limited, Auckland (NZ)

( * ) Notice: Subject to any disclaimer, the term of this patent is extended or adjusted under 35 U.S.C. 154(b) by 167 days.

(21) Appl. No.: 16/465,914

(22) PCT Filed: Dec. 7, 2017

(86) PCT No.: PCT/IB2017/057711
§ 371 (c)(1),
(2) Date: May 31, 2019

(87) PCT Pub. No.: WO2018/104894
PCT Pub. Date: Jun. 14, 2018

(65) Prior Publication Data
US 2020/0069248 A1 Mar. 5, 2020

(30) Foreign Application Priority Data
Dec. 7, 2016 (NZ) .......................................... 727230

(51) Int. Cl.
*A61B 5/00* (2006.01)
*A61B 3/00* (2006.01)
(Continued)

(52) U.S. Cl.
CPC .......... *A61B 5/4863* (2013.01); *A61B 3/0041* (2013.01); *A61B 3/113* (2013.01); *A61B 3/145* (2013.01)

(58) Field of Classification Search
CPC ..... A61B 5/4863; A61B 3/0041; A61B 3/113; A61B 3/145; A61B 5/1114; A61B 3/00; A61B 5/0077; A61B 5/1128
(Continued)

(56) References Cited

U.S. PATENT DOCUMENTS 5,363,154 A 11/1994 Galanter et al.
5,953,102 A 9/1999 Berry
(Continued)

FOREIGN PATENT DOCUMENTS

CN 1541609 A 11/2004
CN 203647468 U 6/2014
(Continued)

OTHER PUBLICATIONS

"International Application No. PCT/IB2017/057711, International Preliminary Report on Patentability dated Nov. 20, 2018", (dated Nov. 20, 2018), 25 pgs.
(Continued)

*Primary Examiner* — Mohammed A Hasan
(74) *Attorney, Agent, or Firm* — Schwegman Lundberg & Woessner, P.A.

(57) ABSTRACT

A system and method for stimulus & eye tracking, useful for the determination of the presence or strength of optokinetic nystagmus (OKN) typically for assessing visual acuity, comprises providing a novel visual stimulus effective to elicit OKN, which includes varying the visibility of a visual stimulus element, or displaying a series of visual stimulus elements so that a later displayed element has different visibility relative to an earlier displayed element. Visual stimulus elements may vanish or appear by reducing or increasing intensity, contrast, size and/or width of the elements or element boundaries. Visual stimulus elements comprise a perimeter that is darker than a background and a
(Continued)

centre that is lighter than the background, and/or a perimeter that is lighter than a background and a centre that is darker than the background.

32 Claims, 9 Drawing Sheets

(51) Int. Cl.
*A61B 3/113* (2006.01)
*A61B 3/14* (2006.01)

(58) Field of Classification Search
USPC .......................................................... 351/210
See application file for complete search history.

(56) References Cited

U.S. PATENT DOCUMENTS

| | | | | |
|---|---|---|---|---|
| 7,918,558 | B1* | 4/2011 | Legerton | A61B 3/113 351/211 |
| 2006/0114414 | A1 | 6/2006 | Mcgrath et al. | |
| 2009/0051877 | A1 | 2/2009 | Delahunt et al. | |
| 2013/0176534 | A1* | 7/2013 | Frankfort | A61B 3/113 351/209 |
| 2013/0278899 | A1 | 10/2013 | Waldorf et al. | |
| 2013/0308099 | A1 | 11/2013 | Stack | |
| 2016/0066781 | A1* | 3/2016 | Thompson | A61B 3/145 600/476 |
| 2018/0249941 | A1* | 9/2018 | Liston | A61B 5/1128 |

FOREIGN PATENT DOCUMENTS

| | | |
|---|---|---|
| CN | 105324794 A | 2/2016 |
| EP | 2984628 A1 | 2/2016 |
| WO | WO-2014168492 | 10/2014 |
| WO | WO-2016081852 A1 | 5/2016 |
| WO | WO-2018104894 A1 | 6/2018 |

OTHER PUBLICATIONS

"International Application No. PCT/IB2017/057711, International Search Report and Written Opinion dated Mar. 1, 2018", (dated Mar. 1, 2018), 12 pgs.

Moke, P. S., et al., "Abstract: Computerized method of visual acuity testing: adaptation of the amblyopia treatment study visual acuity testing protocol", Am J Ophthalmol. Dec. 2001;132(6):903-9, (Dec. 2001), 903-909.

Shah, Nilpa, et al., "Vanishing Optotype acuity: repeatability and effect of the number of alternatives", Ophthalmic Physiol Opt 2011, 31, 17-22. doi: 10.1111/j.1 475-1313.2010.00806.x, (2011), 17-22.

"Chinese Application No. 201780075384.5, First Office Action dated Apr. 6, 2021", (Apr. 6, 2021), 22 pgs.

"European Application No. 17878683.6, Extended European Search Report dated Jul. 10, 2020", (dated Jul. 10, 2020), 8 pgs.

"European Application No. 17878683.6, Response to EESR", (Feb. 5, 2021), 34 pgs.

\* cited by examiner

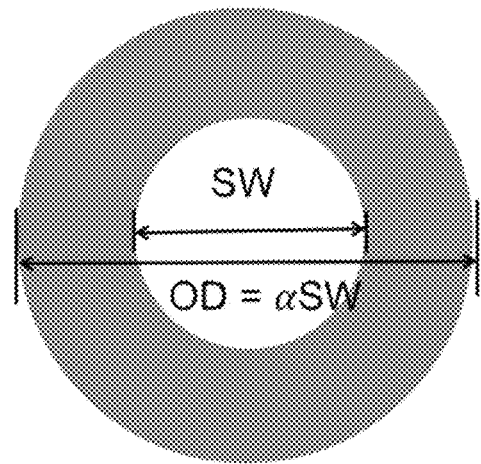
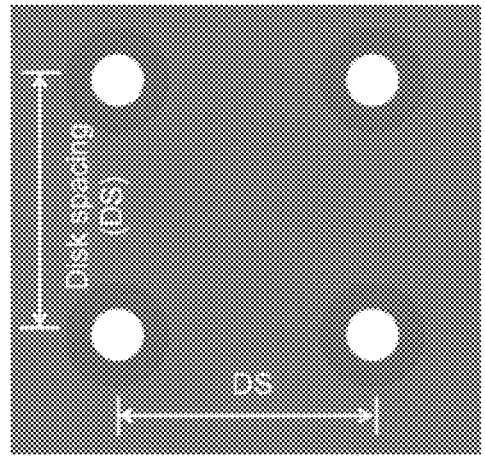
FIGURE 3(a)  FIGURE 3(b)
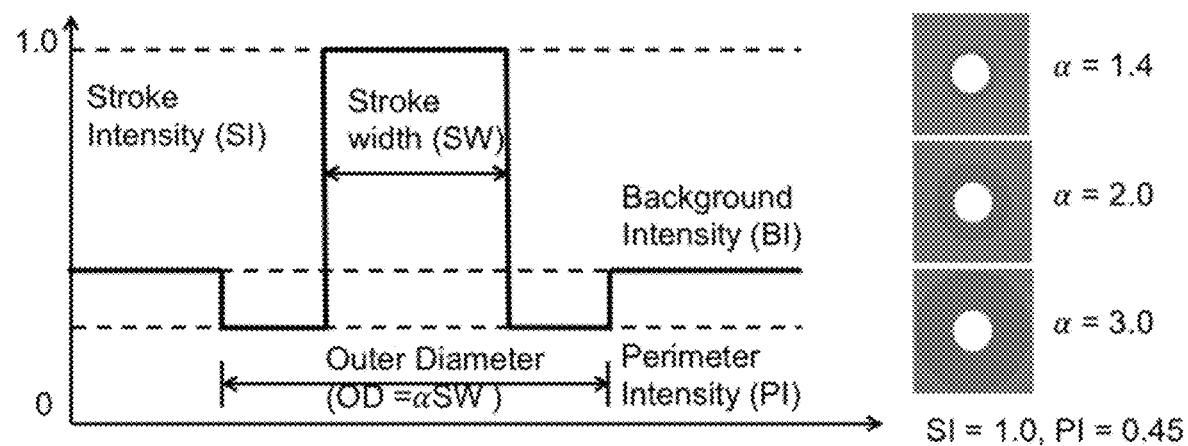
FIGURE 4

STIMULUS AND EYE TRACKING SYSTEM

PRIORITY CLAIM TO RELATED APPLICATIONS

This application is a U.S. national stage filing under 35 U.S.C. § 371 from International Application No. PCT/IB2017/057711, filed on 7 Dec. 2017, and published as WO2018/104894 on 14 Jun. 2018, which claims the benefit under 35 U.S.C. 119 to New Zealand Application No. 727230, filed on 7 Dec. 2016, the benefit of priority of each of which is claimed herein, and which applications and publication are hereby incorporated herein by reference in their entirety.

FIELD OF THE INVENTION

The invention generally relates to a system and method for stimulus & eye tracking, useful particularly but not exclusively for the determination of the presence or strength of optokinetic nystagmus.

BACKGROUND

Accurate evaluation of visual function in young children in particular is challenging. There are few methods available for the direct assessment of perceptual aspects of vision such as visual acuity, motion perception, and stereopsis and/or which are particularly suitable for use by health care providers who do not have extensive training in paediatric ophthalmology, optometry and/or visual electrophysiology.

Optokinetic nystagmus (OKN) is the phenomena of involuntary eye movement triggered by a continuously moving pattern or stimulus, and can be used to evaluate visual function. OKN is the repetition of an eye moving to smoothly pursue a feature in a visual stimulus followed by a resetting event (saccade) where the eye fixes on a new feature of the stimulus. FIG. 1(b) shows a graph of eye displacement over time showing a saw tooth OKN profile that is characteristic of OKN eye movement. The presence or absence of OKN is an objective indication of visual performance and can also be useful for assessing neurological disorders. Early detection of a vision problem in a person's life is also known to significantly improve the outcome of proceeding treatment. The strength of OKN may also be assessed as a useful indicator of visual dysfunction i.e. OKN is present but weak.

In the use of video-oculography techniques for eye tracking and determination of OKN, a visual stimulus is displayed to the subject, and video of the subject's eye(s) is image processed to detect for OKN. International patent application publication WO2014/168492 discloses a method of extracting eye velocity information from video using an optical flow algorithm. The displayed visual stimulus to elicit OKN may consist of high contrast drifting patterns having modifiable properties including contrast, frequency or coherence. Manipulating these parameters allows measurement of the threshold at which OKN is no longer present, or drops below a predetermined threshold for OKN strength. This threshold is a measure of visual performance. Random dot kinematograms consisting of mixtures of solid randomly and coherently moving dots have been used for global motion perception assessment based on OKN responses.

SUMMARY OF THE INVENTION

In one broad aspect the invention consists in a method for stimulus and eye tracking, useful for the determination of the presence or strength of optokinetic nystagmus (OKN), which comprises:
  providing a visual stimulus effective to elicit OKN in front of the eye(s) of a subject by:
    displaying on a display and varying the visibility (as perceived by the subject) of at least one visual stimulus element, or
    displaying a series of at least one visual stimulus element so that a later displayed element has different visibility (as perceived by the subject) relative to an earlier displayed element,
  recording video of the subjects eye(s) viewing the stimulus, and
  image processing the video to detect for OKN.

In one broad aspect the invention consists in an eye tracking system which comprises:
  a display arranged to display and vary the visibility (as perceived by the subject) of at least one visual stimulus element or a series of at least one visual stimulus elements so that a later displayed element has different visibility (as perceived by the subject) relative to an earlier displayed element,
  a camera arranged to record video of the subjects eye(s) viewing the stimulus, and
  an image processing system arranged to image process the video to detect the presence or strength of OKN.

In at least some embodiments varying the visibility of the visual stimulus element(s) comprises causing the visual stimulus element(s) to vanish (as perceived by the subject).

In at least some embodiments at least one visual stimulus element progressively vanishes (as perceived by the subject) on the display, or a later displayed element progressively vanishes (as perceived by the subject) relative to an earlier displayed element. In other embodiments varying the visibility of the visual stimulus element(s) comprises causing the visual stimulus element(s) to increase in visibility or appear (as perceived by the subject). In at least some embodiments at least one visual stimulus element progressively appears (as perceived by the subject) on the display, or a later displayed element progressively appears (as perceived by the subject) relative to an earlier displayed element.

For example varying the visibility of the visual stimulus element(s) or causing the visual stimulus element(s) to vanish may comprise reducing or increasing intensity (optionally including luminescent intensity), contrast (optionally including luminance contrast, chromatic contrast, motion contrast or orientation contrast), size and/or width (spatial frequency) of the visual stimulus element(s) or visual stimulus element boundaries.

In at least some embodiments a spatial content, speed, temporal frequency (flicker), chromatic properties (colour), disparity (3D depth), and rotation or rotational speed of the stimulus (if not rotationally symmetric) of the visual stimulus are varied.

In at least some embodiments the visual stimulus element or elements comprise a perimeter that is darker than a background and a centre that is lighter than the background, and/or a perimeter that is lighter than a background and a centre that is darker than the background. In at least some embodiments the visual stimulus element or elements comprise:

a perimeter having a perimeter boundary that is darker than a background and a centre having a centre boundary that is lighter than the background, and/or a perimeter having a perimeter boundary that is lighter than a background and a centre having a centre boundary that is darker than the background.

In these embodiments, when the boundary lines cannot be resolved they merge together and become indistinguishable from the background. The visual stimulus element is perceived by the subject to vanish or disappear. Alternatively the boundary lines emerge and become distinguishable from the background. The visual stimulus element is perceived by the subject to appear.

In at least some embodiments the visual stimulus elements comprise circle(s) and/or ellipse(s).

In at least some embodiments the visual stimulus element(s) may move across the display and progressively vanish as they move across the display. In other embodiments the visual stimulus element(s) may move across the display and progressively appear as they move across the display.

In embodiments in which providing the visual stimulus comprises displaying a series of at least one visual stimulus element so that a later displayed element progressively vanishes (as perceived by the subject) relative to an earlier displayed element, again the visual stimulus element(s) may move across the display and also may progressively vanish as they move across the display. In embodiments in which providing the visual stimulus comprises displaying a series of at least one visual stimulus element so that a later displayed element progressively appears (as perceived by the subject) relative to an earlier displayed element, again the visual stimulus element(s) may move across the display and also may progressively appear as they move across the display.

In at least some embodiments the visual stimulus element(s) comprise(s) a series of multiple visual stimulus elements.

In at least some embodiments the visual stimulus element(s) comprise(s) upper and lower visual stimulus elements.

In at least some embodiments multiple visual stimulus element(s) move across the display at the same or different speeds.

In at least some embodiments visual stimulus elements move across the display in different directions.

In at least some embodiments visual characteristics of one or more visual stimulus elements alters while visual characteristics of one or more other visual stimulus elements does not.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement or claim, all need to be present but other features can also be present. Related terms such as "comprise" and "comprised" are to be interpreted in the same manner.

BRIEF DESCRIPTION OF THE DRAWINGS

The invention will now be described by way of example only and with reference to the drawings in which:

FIG. 1(a) illustrates the region of an eye typically monitored for change in displacement; FIG. 1(b) shows a graph of eye displacement over time exhibiting a saw tooth profile characteristic of healthy eye movement. FIG. 1(c) shows a graph of eye velocity derived from the eye displacement signal.

FIG. 2(a) is an example image of an eye received from a camera; FIG. 2(b) shows an example of pixel velocity vectors provided by an optical flow algorithm; FIG. 2(c) is an example of a graph of the regional velocity average of the optical flow velocity vectors.

FIG. 3(a) shows a single circle or ellipse stimulus of an embodiment of the invention and FIG. 3(b) shows an embodiment of a visual stimulus which comprises multiple circles and/or ellipses moving across the display in series from left to right or vice versa and in upper and lower rows.

FIG. 4 illustrates an embodiment of a vanishing circle or ellipse stimulus shown as an intensity profile; shown on the right is the appearance of the vanishing optotype as it appears in a localized part of the screen.

DETAILED DESCRIPTION

Stimulus and Eye Tracking

Figure 1:
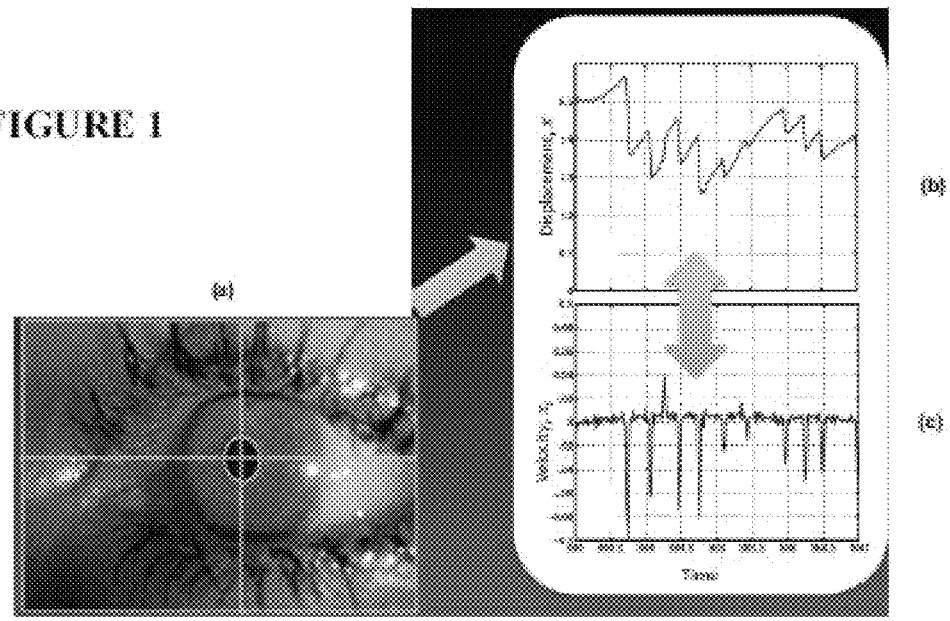
FIG. 1 shows a picture of an eye.

As stated in the method of the invention the visibility of the visual stimulus is varied to enable an evaluation of visual function or make other assessment(s) as referred to subsequently, via OKN. Visibility of the stimuli can be varied by for example the visibility of the stimuli gradually decreasing across a number of trials until the OKN ceases or falls below an OKN strength criterion (descending method of limits). The visibility of the stimuli can be gradually increased from a non-visible level (i.e. the stimuli are in the 'vanished' state for the observer) to the point at which OKN begins or increases in strength above a strength criterion (increasing method of limits). The visibility of the stimuli can be varied following an adaptive staircase algorithm that varies the visibility of the stimului over a series of trials according to the patient's OKN responses and provides an estimated threshold level of stimulus visibility (staircase method). The stimuli can be presented multiple times at a range of visibilities in a predetermined, pseudo-randomized or randomized order. An appropriate function can then be fit to the resulting data that enables the calculation of a threshold visibility (method of constant stimuli). The tester may adjust the stimulus visibility directly using, for example, a dial or touch pad, until the observer's OKN stops or falls below a strength criterion (tester-controlled method of adjustment).

Visual stimulus element(s) may move on the display and their visibility vary as they move, or may be stationary on the display as they vanish. In at least some embodiments the visual stimulus elements comprise circle(s) and/or ellipse(s). Moving visual stimulus elements may move across the display from left to right, from top to bottom, or diagonally across the display. Moving visual stimulus elements may move at the same or different speeds.

A single stationary or moving visual stimulus element or a series of multiple visual stimulus elements may be displayed and vary in visibility. The visual stimulus element(s) may be displayed as a single row or column of static or moving visual stimulus element(s) or upper and lower rows or more rows, or two or more adjacent columns, of visual stimulus elements, for example.

The visual stimulus element(s) may vary in visibility or vanish by reducing in intensity (optionally including luminescent intensity), contrast (optionally including luminance contrast, chromatic contrast, motion contrast or orientation contrast), size and/or width (spatial frequency) of the stimulus element boundaries. In at least some embodiments visual characteristics of one or more visual stimulus elements alters while visual characteristics of one or more other visual stimulus elements does not.

FIG. 3(a) shows a single circle or ellipse stimulus of an embodiment of the invention and FIG. 3(b) shows an embodiment of a visual stimulus which comprises multiple circles and/or ellipses (visual stimulus elements) moving across the display in series from left to right or vice versa and in upper and lower rows. All stimulus elements in upper and lower (or all if more than two rows) may move across the display in the same direction for example from left to right, at the same or different speeds. Alternatively stimulus elements may move in different directions, and for example stimulus elements in an upper row may move across the display in one direction while stimulus elements in another row such as a lower row may move across the display in an opposite direction, at the same or different speeds. Stimulus elements may move from top to bottom of a display or vice versa. Stimulus elements may move diagonally across a display.

In a preferred form a vanishing optotype stimulus (visual stimulus element) comprises a perimeter that is darker than a background and a centre that is lighter than the background, and/or a perimeter that is lighter than a background and a centre that is darker than the background. In at least some embodiments the perimeter has an outer diameter or transverse dimension OD=αSW and thickness SW(1−α)/2 wherein SW is a diameter or transverse dimension of the centre and a is in the range 1-5 or more preferably 1 to 3.

A single vanishing disk stimulus element is shown by itself in FIG. 3(a), and as part of an array in FIG. 3(b) where it has been over-layed on a background. FIG. 4 on the right hand side shows a vanishing stimulus element—as it vanishes reduces from 3.0 to 0. FIG. 4 on the right hand side shows the vanishing stimulus element with a initially=3.0, and then also at α=2.0 and at α=1.4.

The diameter or transverse dimension (the stimulus element may not be circular) SW may be regarded as the stroke-width of the stimulus element, specified in log MAR. This centre is surrounded by a perimeter or annulus which may be of constant thickness SW(1−α)/2, the stated formulae resulting from considering the central disk (width diameter SW) as overlaying the surrounding outer disk with diameter OD=αSW. The stimulus shown to the observer may be an array of such vanishing disks that cover the screen. The horizontal and/or vertical centre-to-centre spacing DS may be for example in the range 1 to 10 or more preferably 2 to 6×the diameter or transverse dimension SW of the stimulus element, and the entire array drifts across the screen either leftwards or rightwards at a constant angular velocity for the entirety of the duration of a presentation.

In the examples shown in FIG. 4 the initial or starting intensity SI of the centre is lower than that PI of the perimeter. The background intensity BI is between that of the perimeter and centre. For example BI may initially be about half of PI. Another possible intensity profile is shown in FIG. 4. As stated, in the three specific examples on the right hand side of FIG. 4 α=1.4, α=2.0 and α=3.0. In each case SI=1.0, PI=0.45, and BI=0.5. Where the perimeter is darker than the centre then for example PI may be between 0 to 0.5 of maximum intensity, SI between 0.5 to 1.0 of maximum intensity, and BI between 0.4 to 0.6 and typically about 0.5 of maximum intensity. Example ratios are SI/PI/BI of 0.9/0.45/0.5 and 0.75/0.45/0.5.

Alternatively instead of reducing or increasing in intensity or luminescent intensity, the contrasting perimeter may reduce in size and/or vanish or increase in size and appear (as perceived by the subject), as the circle(s) and/or ellipse(s) move across the display. The centre may remain substantially constant. FIG. 4A shows a single circle or ellipse stimulus of an embodiment of the invention and FIG. 4B shows an embodiment of a visual stimulus which comprises multiple circles and/or ellipses (visual stimulus elements) moving across the display in series from left to right or vice versa and in upper and lower rows. In one option some stimulus elements, such as stimulus elements in one row, may be caused to vanish or appear as they move while other stimulus elements, such as stimulus elements in another row, do not. This may enable assessment of a direction that OKN goes in, which may allow for the assessment of discrimination between visible stimuli—known as the just noticeable difference.

Figure 5:
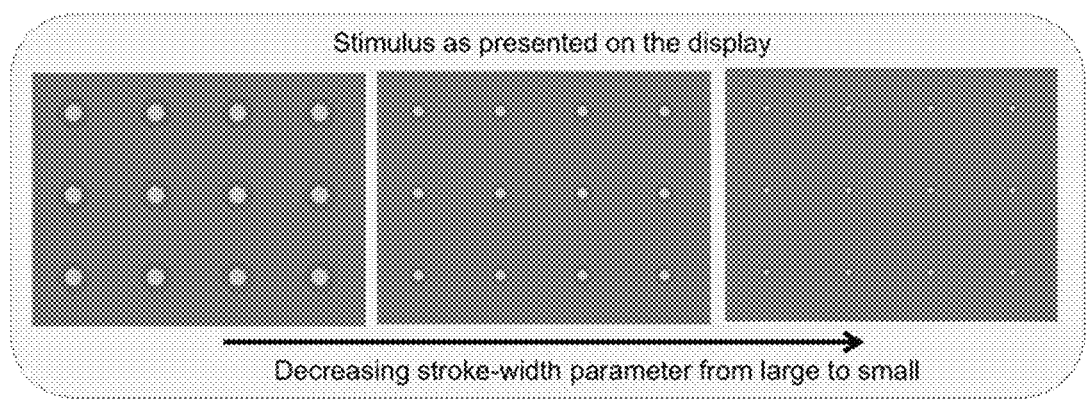
FIG. 5 shows an embodiment of a visual stimulus which comprises multiple disk visual stimulus elements moving across a display in series from left to right in three rows, at three stroke-width stimulus levels, with the stroke-width decreasing from high to low.

FIG. 5 shows an embodiment of a visual stimulus which comprises multiple disk visual stimulus elements moving across a display in series from left to right in three rows, at three stroke-width stimulus levels, with the stroke-width decreasing from high to low (going from left to right). The aim of visual acuity testing is to determine the stroke-width value at which the observer cannot detect the presence of the presented field.

Figure 6:
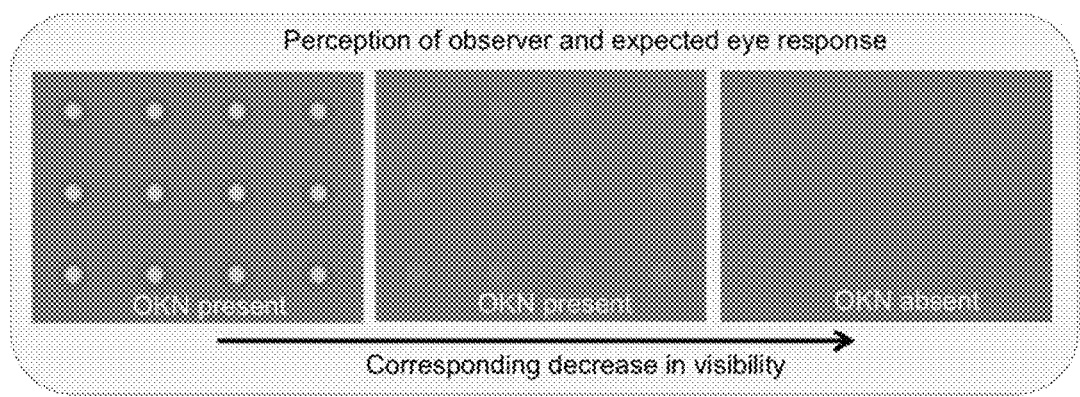
FIG. 6 shows the expected perception of the observer possessing refractive error, of the stimulus of FIG. 5.
Figure 7:
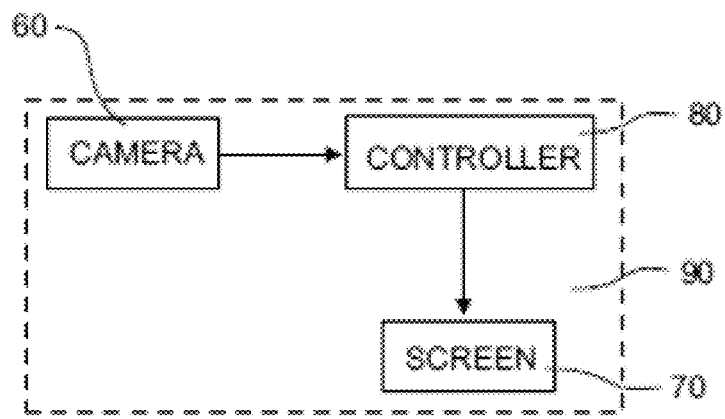
FIG. 7 shows an overview of the components of a system including a camera, screen and a computational device.

FIG. 6 shows the expected perception of the observer possessing refractive error. In this case the perception of the stimuli presented in FIG. 5 is now degraded in all cases. The perception by the observer is that the disks are visible but progressively more difficult to detect as the stroke-width parameter is reduced. In this example, it is seen that the field of disks has vanished completely at the smallest stroke-width parameter setting (the right-most panel of FIG. 5). The threshold of detectability has been passed, and the subject's OKN response has disappeared (as indicated by "OKN absent" on the right-most panel of FIG. 6). In both figures it is noted that the field of disks would be moving in a fashion (for example, drifting continuously either leftward or rightward) designed to induce a robust OKN response in the presence of a detectable stimulus pattern.

In addition, a spatial content, speed, temporal frequency (flicker), chromatic properties (colour), disparity (3D depth), and rotation or rotational speed of the stimulus (if not rotationally symmetric) of the visual stimulus may be varied as the circle(s) and/or ellipse(s) move across the display.

The visual stimulus to elicit OKN may be displayed on a VDU of any suitable size and resolution for example an LED or LCD display. The display may be placed at a distance of approximately about 0.5 to 6 m from the subject's eyes for example. Video footage is collected using a digital camera (RBG or infrared), preferably located proximate the display to present a clear line of sight to view the eyes.

To improve the attention of young test subjects, the visual stimulus video may be interspersed with a video segment that appeals to children, such as a cartoon. A cartoon or other kind of animated video is displayed for a period of time adequate to gain the attention of a young subject before the visual stimulus video is displayed for a period of time adequate to acquire OKN data. The cartoon can be displayed when attention wanes or alternatively when the OKN video has finished. The cartoon may be switched to and from the display automatically by a control device or manually by an operator.

Video image processing is used to detect whether or not the stimulus has elicited OKN, or the strength of OKN, in a subject's eye. The stimulus parameters at the threshold where OKN is no longer detected or OKN falls below a particular strength provides an indication of visual performance. A clinician may review the information determined from the eye movement. Alternatively, a statistical analysis process may be applied to the extracted information to determine the presence or absence of OKN.

The video processing to detect OKN may be of recorded video footage or in real time.

Some embodiments further comprise a visual stimulus arranged in front of the eye, the stimulus operable to elicit optokinetic nystagmus.

Some embodiments further comprise comparing the average velocity information to known optokinetic nystagmus velocity information to make a determination of the health of an eye in response to the stimulus.

The system may be implemented as a dedicated instrument, in portable or handheld device having both a camera and a computational power, such as a smart phone, tablet or laptop device, for example. FIG. 5 shows an overview of the components of the system including the camera 60 for recording the eye footage, a screen 70 for displaying the stimulus and a computational device 80.

Image Processing and OKN Detection

Video processing for OKN detection or assessment may comprise extracting eye velocity and/or displacement information from video, using for example an optical flow algorithm or a point tracking algorithm. The video footage is used to make an estimate of the velocity and/or displacement, of an eye as a subject watches the visual stimulus, such as determining a velocity and/or displacement estimate of pixels inside the coarse determination of a limbal region and/or pupil region of an eye by application of an image processing algorithm known as optical flow and/or point tracking. In preferred embodiments, a Lucas-Kanade optical flow algorithm and/or a Kanade-Lucas-Tomasi (KLT) or other point tracking algorithm may be used. The velocity and/or displacement estimate provided by the optical flow and/or point tracking algorithm is an average of the pixel velocities and/or displacement in the coarsely determined limbal and/or pupil region. Heuristic analysis and/or template matching algorithm may be applied to the displacement and/or velocity estimate to determine the presence and direction of OKN. The velocity and/or displacement estimate information may also be manually compared to healthy eye velocity and/or displacement information, and in particular the velocity threshold at which OKN is no longer present, or drops below a predetermined threshold for OKN strength, to make a comparative judgement of the function of the eye and/or the visual pathway. The velocity and/or displacement estimation may also be used to track the direction of a person's gaze. The direction of the gaze may be used to judge behavioural characteristics of a person including information such as what visual stimulus gains their attention. In some embodiments the optical flow and/or KLT algorithm is applied to determine pixel velocity and/or displacement information between consecutive frames of a length of video footage corresponding to several reset events.

The method of determining OKN according to various embodiments is conducted according to the following steps. A video sequence containing footage of the eye is recorded while the eye watches a stimulus. In some embodiments, the video footage is reduced to grey scale to reduce computation complexity. An optical flow and/or point tracking image processing algorithm is applied to the video footage to determine pixel velocity and/or displacement information from sequential frames. The velocity and/or displacement information is determined from a limited region of the eye and that region is the limbus and/or pupil and/or limbal edge portion of the eye. The region is a coarse estimate of the limbal and/or pupil region of the eye determined by an edge detection and/or thresholding algorithm. The image processing algorithm outputs optical flow and/or point tracking information represented by pixel velocity and/or displacement information in determined the limbus and/or pupil region of the eye over two consecutive frames in the video footage. The pixel velocity and/or displacement information, including the speed, displacement and direction, can be directly assessed to determine the presence and direction of OKN.

Figure 8:
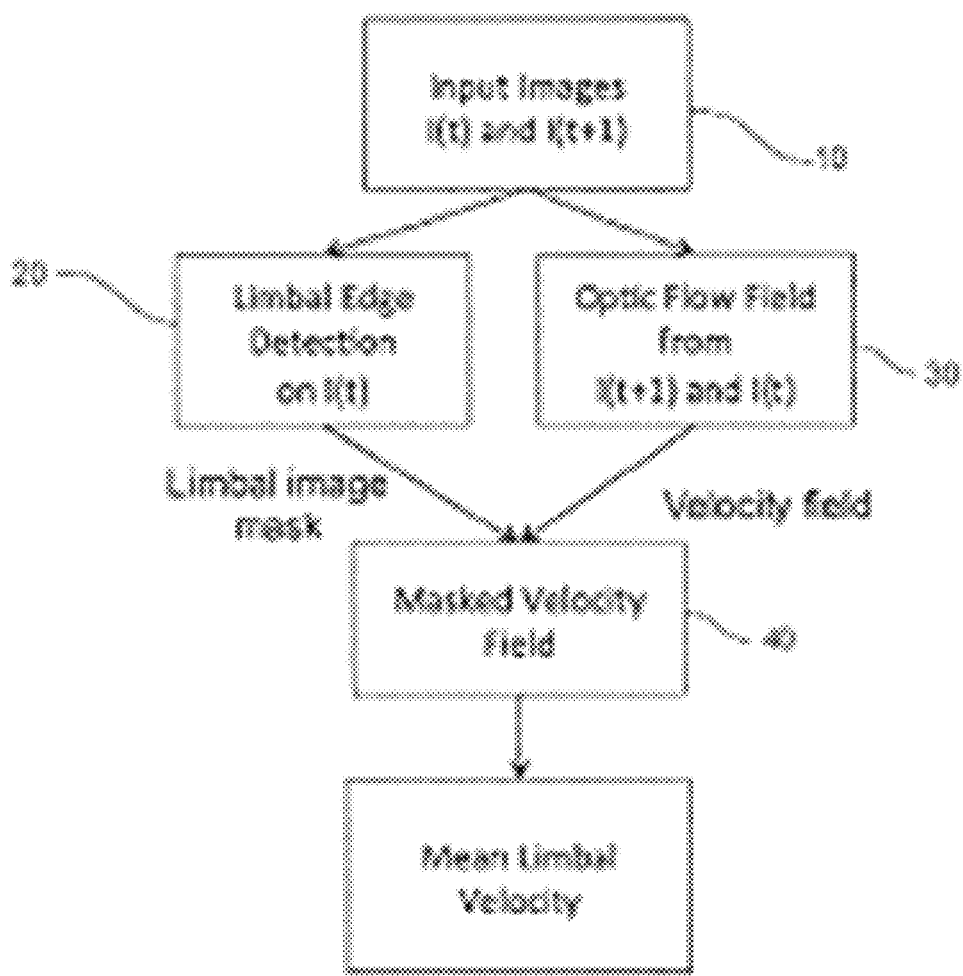
FIG. 8 is a flow chart of steps in video processing for OKN detection or assessment in one form.

One example of the steps of the process is shown in FIG. 8 where the transformation of two consecutive image frames into an estimate of pixel velocity is shown. In a first step 10, consecutive video frames I(t) and I(t+1) are taken from high definition colour video footage and reduced to gray scale. In a second step 20, a coarse determination of the limbal region of the eye is determined by an edge detection process applied to the video footage to determine an edge map. The edge map represents a determination of the location of the limbus portion of the eye and therefore the area of the video footage from which optical flow information is to be determined. The edge map does not need to be precisely determined for the optical flow information to be useful. The process is robust to variation in the limbal edge maps obtained throughout frames in the video footage. The edge detection is ideally performed by application of a Prewitt operator with hysteresis thresholding. However, those skilled in the art will recognise other edge detection strategies or operators could be used to determine the limbal region. Connected regions under a certain weight and regions connected to the image border are removed. In a third step 30, which may be processed concurrently or before the second step 20, an optical flow estimation process determines pixel velocity information from spatial and temporal changes in pixel intensity. As shown in FIG. 1(c), a limbal region should exhibit a velocity spike during a rapid resetting event of an eye (saccade) and smooth or constant velocity changes during other periods when a stimulus is being observed.

Figure 2:
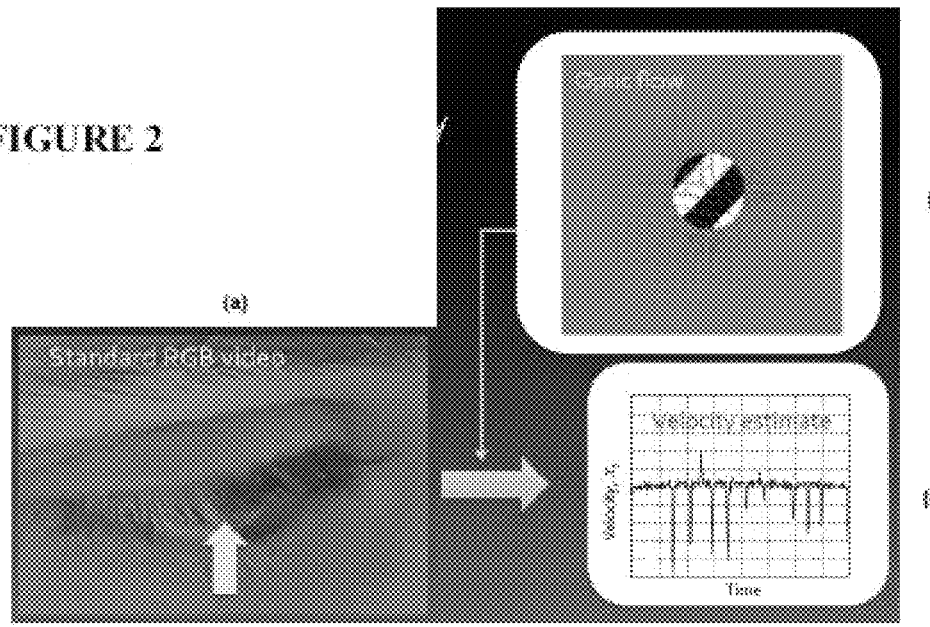
FIG. 2 shows an example where consecutive image frames are transformed into an estimate of pixel velocity.

FIG. 2 shows the optical flow process in greater detail. FIG. 2(a) shows an image or single frame of a piece of video footage showing an eye. FIG. 2(b) shows a number of vectors indicating the magnitude and direction of pixel travel between consecutive frames. FIG. 2(c) is a graph of the average velocity of the pixel vectors of FIG. 2(b) for a number of consecutive frames.

In the fourth step 40 of FIG. 8, the limbal region information provided by the edge detection process 20 is combined with the pixel velocity information provided by the optical flow process 30 to produce a masked velocity field. The masked velocity field represents velocity information only within the detected limbal region. In a fifth step 50, the velocity information from the masked velocity field is averaged to produce a velocity value for a given pair of consecutive frames in the video footage. The process of FIG. 6 is performed on as many consecutive frames in the video footage as desired such that a graph of velocity is provided as a function of time. The graph can then be analysed to determine OKN information.

Further information is given in international patent application publication WO2014/168492 the entire contents of which are incorporated herein by reference.

Figure 9:
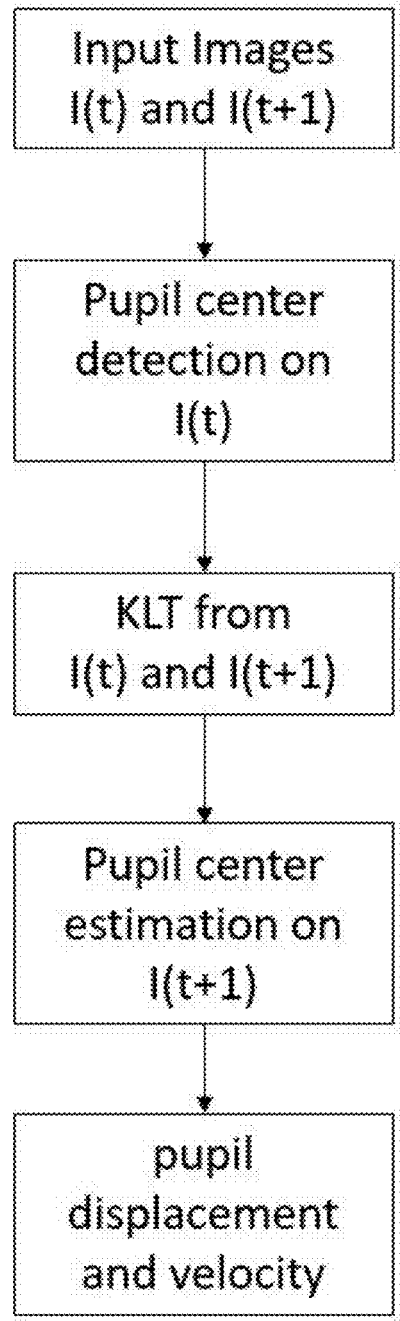
FIG. 9 is a flow chart of steps in video processing for OKN detection or assessment in another form.
Figure 10A:
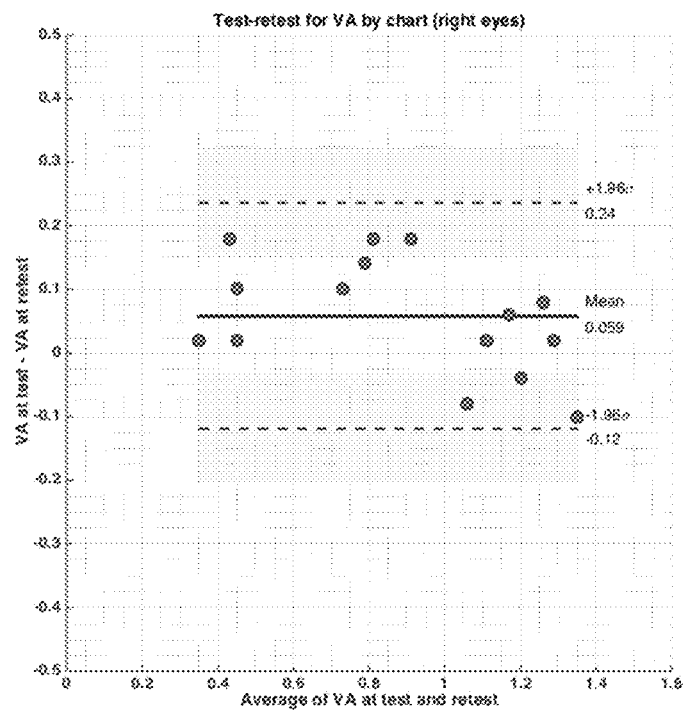
FIGS. 10(a) and 10(b) are Bland-Altman plots referred to in the subsequent description of experimental work.
Figure 10B:
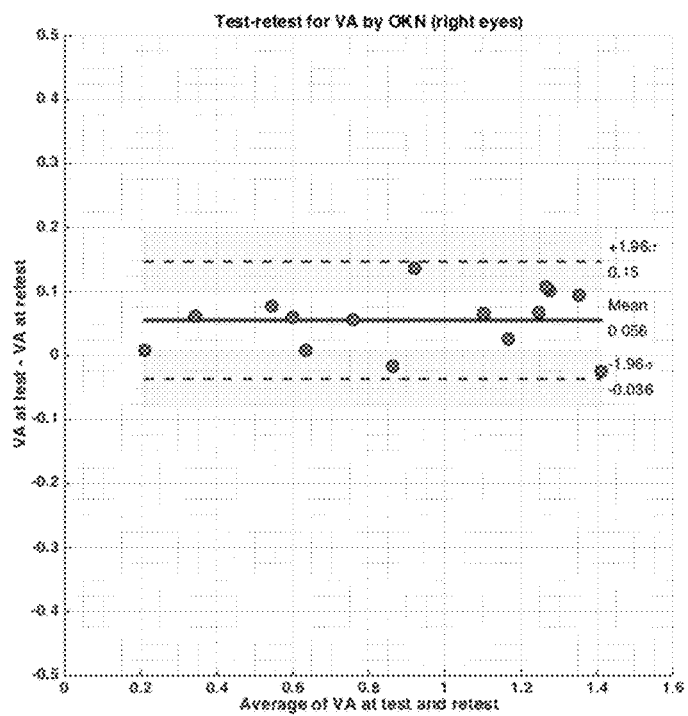

Another example of the steps of the process is shown in FIG. 9 where the transformation of two consecutive image frames into an estimate of pixel displacement and velocity is shown. In a first step 10, consecutive video frames I(t) and I(t+1) are taken from high definition colour and or infrared video footage and reduced to gray scale. In a second step 20, a coarse determination of the pupil region and pupil centre of the eye is determined by a thresholding algorithm and morphological operations applied to the video frame. The KLT algorithm estimates the new location of pupil centre in video frame I(t+1) based on changes in pixel intensity. By extracting pupil centre in two consecutive frames, displacement and velocity signal of pupil/eye can be determined.

These techniques are substantially robust against the error induced by head movements seen in normal adult fixations, eye blinks, reflections and other error inducing factors. Further, these techniques may be combined with head stabilisation for use with young children or subjects who would not tolerate head mounted equipment. These techniques are therefore video-oculography techniques readily applicable to infants or young children who would otherwise be unable to be assessed. These techniques may be implemented with standard 'off the shelf' video equipment thereby avoiding the need for expensive supporting hardware. The velocity and displacement information, graphs resulting from the above described techniques can be analysed directly by a trained clinical professional and/or further processed by an OKN detection process that will now be described.

OKN strength can be determined by the following. Peaks not indicative of OKN are rejected, for example, by comparing them to a threshold and discarding those peaks below the threshold. An average of the heights of the surviving peaks is determined and scaled by an appropriate normalization value $1/\sigma_P$. A low value will result if peaks are weak or equally distributed between positive and negative. Conversely, if peaks are consistently positive or negative, the measure will scale with the average height, and the sign will correlate with the direction of the reset event.

A more detailed explanation of the process step for detection of OKN from the obtained velocity information is given in international patent application publication WO2014/168492.

Furthermore, a template matching algorithm is used to determine presence and direction of OKN from displacement signal. Dynamic time warping (dtw) algorithm is used to find the sawtooth pattern in the displacement signal. Two sawtooth templates are applied to detect both left and right direction OKN.

Optionally head trajectory information is used to improve the eye velocity and/or displacement information, by offsetting head trajectory information against the eye tracking information to substantially remove eye velocity and/or displacement information caused by head movement. For example, data relating to the velocity and/or displacement of head movement can be offset against data relating to eye movement so error caused by non-zero head velocity and/or displacement is substantially reduced or removed from the eye velocity and/or displacement information.

As stated the system and method of the invention are useful for assessing the presence or strength of optokinetic nystagmus, the presence or absence of which is an objective indication of visual performance and can also be useful for assessing neurological disorders. The invention may be useful also for assessing any one or more of the presence or absence or quality of colour vision, depth perception (stereopsis), motion perception, traumatic brain injury, dyslexia, concussion, contrast sensitivity, ADHD, dizziness/balance, fatigue, cognitive function, neurological disorder, multiple sclerosis, child development disorder, anything that interferes with the visual pathways of the brain, mental health disorder, anxiety, depression, sensory processing disorder, or neurodegenerative disorder such as Parkinson's and/or Alzheimer's Disease.

Experimental

We tested the ability of a vanishing disk based stimulus to estimate visual acuity as determined by an ETDRS visual acuity chart. We found a better test-retest reliability for the testing based on OKN versus than that of the visual acuity chart. We found a robust correlation ($R^2=0.9$) between the ETDRS and OKN visual acuity data, across a cohort of adults with uncorrected refractive errors (in the right eye only). The line of best fit after recalibration yielded "fitted" minimum sensitivity of the test (c) which was −0.01 log MAR, whilst the agreement with the visual acuity (m) was 1.04 log MAR by OKN method/log MAR by VA chart. A second experiment was conducted in which blurring was used to test the range from 0.0 to 0.5 log MAR. Two stimulus parameter settings were tested, giving good linear fitting results of $R^2=0.76$ and 0.86 respectively. The fitted line coefficients were (m=0.62, c=0.05) and (m=0.50, c=0.21). The thinner stimulus had the best fitted minimum sensitivity and improved agreement with the visual acuity chart overall, whilst the thicker stimulus had the worst sensitivity (c=0.21) and the lowest agreement (m=0.50) overall. Overall we found a linear relationship between visual acuity using OKN and ETDRS, and furthermore we were able to manipulate the optokinetic response, by only adjusting the alpha parameter.

Experiment One: Visual Acuity Testing with Refractive Error

Method Participants: Healthy participants (N=18, Average age=29±6 years) were recruited through the School of Optometry and Vision. Science.

Baseline visual acuity by ETDRS VA chart: Because it was expected that the eyes performance for a particular individual would be correlated, only data for right eyes was included for analysis in this experiment. Participants were instructed to stand 3 metres from the ETDRS-type VA chart (AT-20P Medmont Acuity Tester, Medmont Pty Ltd, Australia) and to read letters starting from larger letters at higher log MAR levels (maximum size log MAR 1.3) down to smaller letters at lower log MAR levels (minimum size log MAR −0.3) in 0.1 log MAR decrements (5 letters per log MAR level). The scoring was done by recording firstly the smallest complete line read, followed by deducting an extra 0.02 log MAR for every letter read correctly from the smaller partially read lines. A smaller log MAR score corresponded to smaller resolvable detail and better VA. The duration of VA measurement by ETDRS chart was approximately 15 minutes per participant per testing session.

Data collection and analysis of OKN data: Vanishing disk stimulus arrays ($\alpha=2$, SI=0.75, PI=0.45) were used for this experiment. Array patterns were shown over 5 seconds trials during which they drifted in a randomly determined direction (leftwards or rightwards, with a constant speed of 5 degrees/second). The stroke width (SW) parameter varied in 0.1 log MAR steps over the range of 1.0 to 0.0 log MAR with stimulus having stroke-width set in accordance with the design of standard ETDRS visual acuity (VA) charts. A total of 11 levels (1.0 to 0.0 log MAR in steps of 0.1 log MAR) were tested in descending order. Each log MAR level was presented five times to match the number of letters on each line of the ETDRS chart. Henceforth an OKN 'line' refers to five trials of the same log MAR value. This allows for common terminology between the ETDRS chart and the OKN measure. Each OKN stimulus presentation was randomized to drift rightwards or leftwards. The total experiment therefore consisted of 55 trials each lasting 5 seconds. All participants were tested with the ETDRS Chart and OKN stimulus and then re-tested on a different day.

VA scoring by OKN: An experienced observer performed the following steps to determine the best OKN by subjective observation. Starting from the videos with the largest disk stimulus (log MAR 1.0), the observer reviewed videos so as to find the lowest line where the participant obtained OKN in all five videos (for a particular log MAR). This defined the initial base line. For each video after the initial baseline videos (continuing in descending log MAR) the baseline log MAR was reduced by 0.02 log MAR if OKN was judged to have been observed in it. For practical purposes this continued until no OKN was observed in all five trials belonging to a line (thereby defining the "bottom line"). The final VA reported was the baseline with 0.02 subtracted for all videos showing OKN.

VA recalibration of OKN: The OKN visual acuity data was calibrated to assess whether thresholds for a particular OKN log MAR could match the ETDRS chart equivalent. A linear fit derived from the raw experimental data (VA by ETDRS chart versus VA by OKN) was used to rescale the visual acuity by OKN data. This involved adding the difference between the fitted line and the required line (the line of slope 1 passing through the origin) at a particular VA by chart value to the raw VA by OKN.

Results

Figure 11:
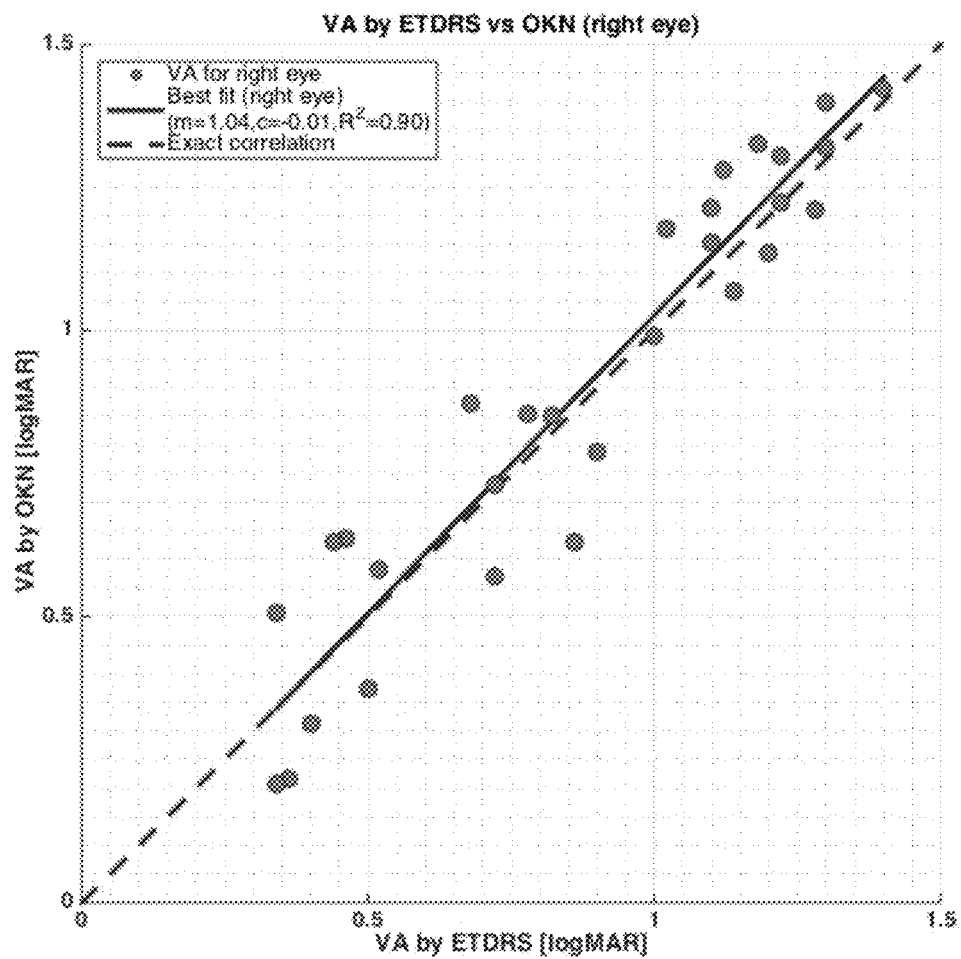
FIG. 11 is referred to in the subsequent description of experimental work and shows a correlation obtained between the visual acuity measured using a gold-standard ETDRS chart versus the visual acuity determined by OKN for trial participants not wearing their usual optical correction (henceforth referred to as being uncorrected). A rescaling of the OKN data has been applied.
Figure 12:
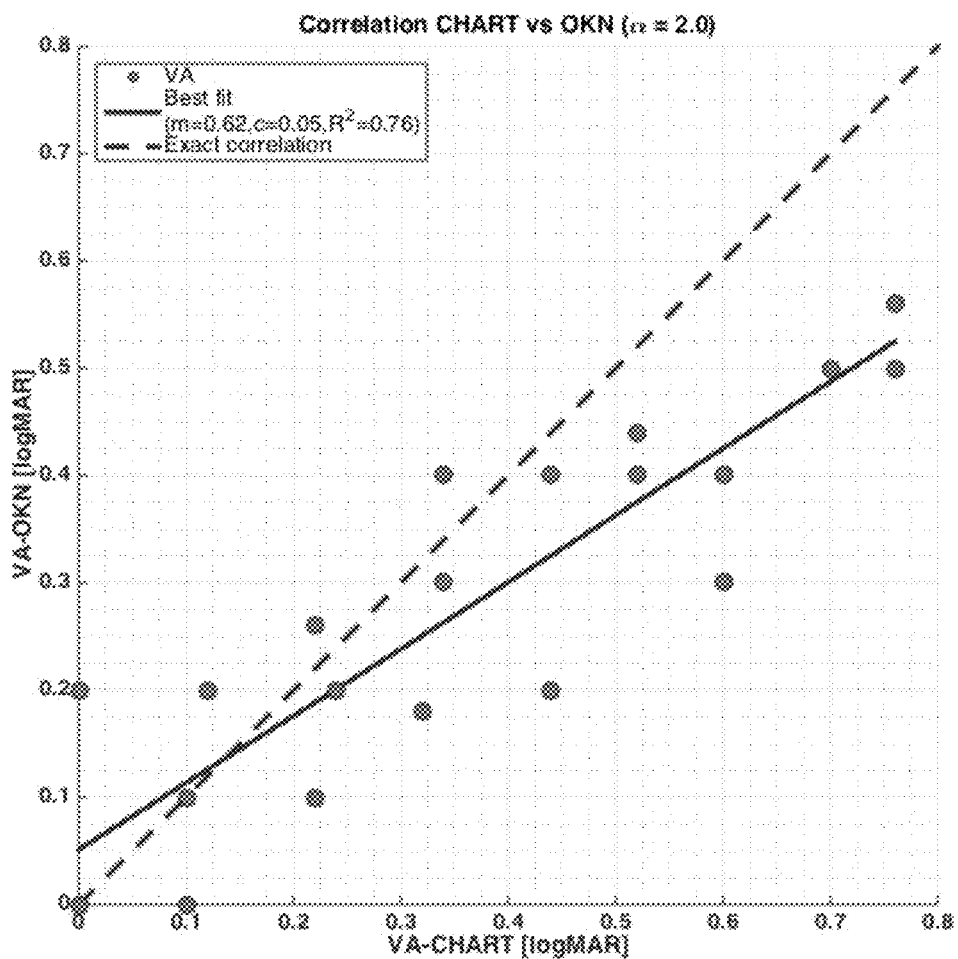
FIG. 12 is referred to in the subsequent description of experimental work and shows a correlation with visual acuity as determined by OKN (vertical axis) and the ETDRS chart (horizontal axis) for blurring of, two trial participants. No rescaling of the OKN has been applied in this case.

FIG. 11 contains Bland-Altman plots for the ETDRS visual acuity chart and the visual acuity as determined by OKN, for the test session and the retest session showing the test and the retest results. The mean difference for the ETDRS chart was 0.059 and the limits of agreement were 0.12 and 0.24 respectively ($1.96\sigma=0.18$). The mean difference of the OKN based chart was 0.056 and the limits of agreement were −0.036 0.15 ($1.96\sigma=0.09$). The results indicated a better test-retest performance for the OKN based method than the chart. FIG. 12 shows the correlation obtained between the visual acuity chart obtained by ETDRS chart versus the visual acuity determined by OKN for uncorrected participants (applied to right eyes, pooled over both the test and retest data). The results indicate good agreement between the two VA measures (a high R-squared coefficient of 0.90) and agreement with the line of best correlation, with an estimate slope of 1.04 and y-intercept c=−0.01.

Experiment Two: Added Blur Protocol

The range of uncorrected visual acuities found for the ETDRS chart in experiment one was 0.32 to 1.40 (median=0.88, IQR=[0.61, 1.18]). However, we were interested in assessing performance for a lower range of logMARs 0.0 to 0.3 because of its clinical significance. Therefore we sought to repeat the protocols described in experiment one, for observers who were intentionally blurred to produce visual acuities inclusive of this range. We tested also the effect of changing the parameter, so the experiments were repeated for $\alpha=2$ and $\alpha=3$.

Method

Participants: Healthy participants (N=2, Average age=30) who were part of the research team participated. A baseline refractive correction was determined by subjective refraction. Visual acuity deficit (blurring) in the right eye was then simulated in the two observers by adding plus powered trial lenses to the baseline correction, in +0.25D steps, whilst covering the eye not being tested. The blurring end-point was the highest dioptric power of plus lenses required to reduce visual acuity to ≥log MAR 0.6. Visual acuity at each blurring step was measured by ETDRS VA chart (AT-20P Medmont Acuity Tester, Medmont Pty Ltd, Australia) as described in experiment one.

The protocol described by experiment one was repeated here except in addition to the optotype ($\alpha=2$, SI=0.75, PI=0.45) we also tested a second optotype ($\alpha=3$, SI=0.75, PI=0.45). This has been denoted thin and thick in the graphs but would be renamed in the future. Furthermore, there was no recalibration as performed in the presentation of data from experiment one.

Results

Figure 13:
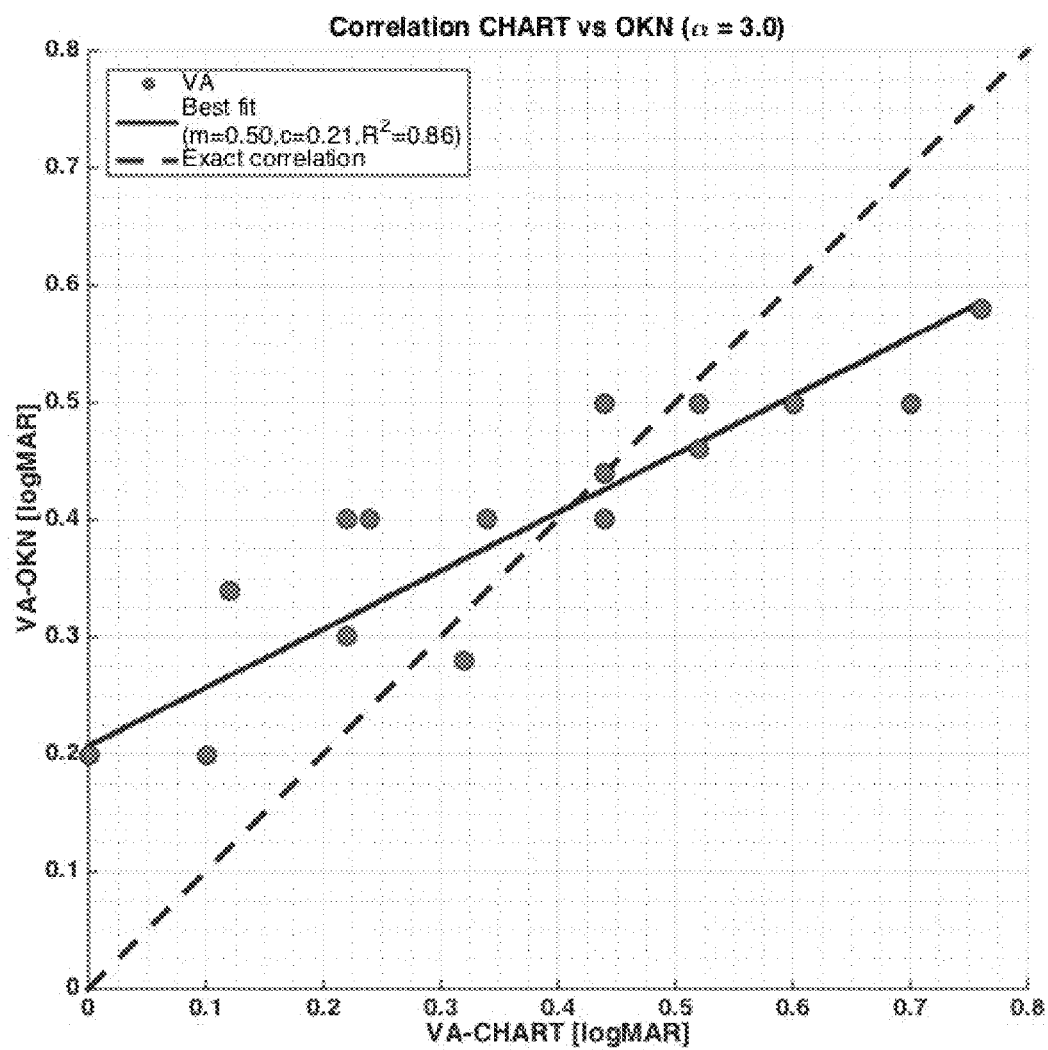
FIG. 13 is referred to in the subsequent description of experimental work and shows a correlation with visual acuity as determined by OKN (vertical axis) and the ETDRS chart (horizontal axis) for blurring of two participants, using a larger alpha parameter. No rescaling of the OKN has been applied in this case.

The correlations for VA by OKN vs VA by chart for stimuli with $\alpha=2$ and $\alpha=3$ are shown in FIGS. 12 and 13. Calibration was not applied as in experiment one, so comparison across the two could be made. Nevertheless, the raw (uncalibrated) linear fitting results were good ($R^2=0.76$ and 0.86 respectively). The slopes of the fitted lines were comparable (m=0.62 for $\alpha=2$, versus m=0.50 for $\alpha=3$) with the difference equivalent to a 0.12 log MAR difference in VA by OKN across a change of 1 log MAR in VA by chart. The main difference was that thicker stimulus results were shifted vertically along the vertical axis, with a minimum sensitivity of c=0.21 log MAR (versus c=0.05 log MAR for α=2). As a result, it was observed that the fitted line, and therefore the data, was shifted so as to cross the line of best correlation (i.e., the position where the best agreement with the VA chart occurs) at a higher VA by chart threshold. In FIG. 11 this occurred at 0.12 log MAR, whilst in FIG. 12 this occurred at 0.41 log MAR. This observation suggests that the stimulii have a "best" operating point, that can be modified by appropriate selection of the α parameter.

Experiment 3: Adult Clinical Trial

Purpose: The purpose of this study was to assess the level of agreement between the Objective. Acuity OKN system and stimulus compared with standard letter chart measurements of monocular visual acuity in a group of adults. Measurements were made with no refractive correction and with full correction for refractive error. These measurements were made using an automated ETDRS Visual Acuity Chart and the OKN Visual Acuity System.

Subjects: 93 participants were recruited with the clinical site being the Southern College of Optometry, Memphis, USA.

Stimuli: Moving stimuli were presented on a 27 inch DELL S2716DG LED monitor, placed 3 meters away from the subject to elicit OKN. The stimuli was patterned disk shaped circles, consist of a bright inner circle and a darker outer ring. Other controlled parameters include disk size, space, and moving speed. The table below explains the characteristics of each stimulus at each level:

ETDRS Visual Acuity Chart: Adult visual acuity was tested by qualified optometrist at 3 meters distance with an automated ETDRS visual acuity chart. The ETDRS results were collected separately from OKN, to make sure that the OKN analysis was masked from the ETDRS results. An independent statistician analysed the data.

Data Analysis: Each video was analysed offline using automated head and eye tracking algorithms to extract eye movement data. The presence or absence of OKN in each trial was determined using an OKN detection algorithm, with present indicating a positive result.

The method used to detect visual acuity was:

Step 1: Find the lowest line with at least three OKNs, as the initial baseline. Then find the lowest line with at least two OKNs as bottom line. If the initial baseline and the bottom line are within two lines, initial baseline=final baseline. If the difference is more than three lines, keep looking for the lowest line with at least two OKNs as the baseline.

Step 2: Visual Acuity Score=final baseline−N×0.02, N=Number of OKNs below the final baseline.

Results:

There was a significant positive correlation between the measurements made with the OKN Visual Acuity System and those made with the ETDRS chart (Pearson correlation coefficient 0.787, p<0.0001). This indicates that the OKN-based measures are well correlated with the ETDRS measures and that the OKN Visual Acuity System can effectively, assess visual acuity.

| # Syntax: | Note (displayed to operator) | Central intensity (inner contrast) | Perimeter intensity (outter contrast) | Field spacing (degree) | Stroke width (logMar) | Speed (degree/sec) | Disk type (outter/inner) | Direction (come from) | Ramp duration (acceleration duration/seconds) |
|---|---|---|---|---|---|---|---|---|---|
| Fixation | 2 | | | | | | | | |
| Disk | Disk presentation 1 (from left) | 0.75 | 0.45 | 0.5 | 1 | 5 | Disk_2:1 | Left | 1 |
| Fixation | 2 | | | | | | | | |
| Disk | Disk presentation 2 (from right) | 0.75 | 0.45 | 0.5 | 0.9 | 5 | Disk_2:1 | Right | 1 |
| Fixation | 2 | | | | | | | | |
| Disk | Disk presentation 3 (from left) | 0.75 | 0.45 | 0.5 | 0.8 | 5 | Disk_2:1 | Left | 1 |
| Fixation | 2 | | | | | | | | |
| Disk | Disk presentation 4 (from right) | 0.75 | 0.45 | 0.5 | 0.7 | 5 | Disk_2:1 | Right | 1 |
| Fixation | 2 | | | | | | | | |
| Disk | Disk presentation 5 (from left) | 0.75 | 0.45 | 0.5 | 0.6 | 5 | Disk_2:1 | Left | 1 |
| Fixation | 2 | | | | | | | | |
| Disk | Disk presentation 6 (from right) | 0.75 | 0.45 | 0.5 | 0.5 | 5 | Disk_2:1 | Right | 1 |
| Fixation | 2 | | | | | | | | |
| Disk | Disk presentation 7 (from left) | 0.75 | 0.45 | 0.5 | 0.4 | 5 | Disk_2:1 | Left | 1 |
| Fixation | 2 | | | | | | | | |
| Disk | Disk presentation 8 (from right) | 0.75 | 0.45 | 0.5 | 0.3 | 5 | Disk_2:1 | Right | 1 |
| Fixation | 2 | | | | | | | | |
| Disk | Disk presentation 9 (from left) | 0.75 | 0.45 | 0.5 | 0.2 | 5 | Disk_2:1 | Left | 1 |
| Fixation | 2 | | | | | | | | |
| Disk | Disk presentation 10 (from right) | 0.75 | 0.45 | 0.5 | 0.1 | 5 | Disk_2:1 | Right | 1 |
| Fixation | 2 | | | | | | | | |
| Disk | Disk presentation 11 (from left) | 0.75 | 0.45 | 0.5 | 0 | 5 | Disk_2:1 | left | 1 |

Test Procedure: OKN Test: For the OKN part of the trial participants viewed 11 different levels of the stimulus from 3.0 m. Five trials of each stimulus level were used, with each stimulus lasting 6 sec. Each stimulus level represented a log MAR level. The log MAR levels tested were from 1-0 log MAR. Adult eye movements were recorded using an IDS UI-3140CP infrared camera with a resolution of 1280×1024 pixels. There were 100 participants who wore glasses or contact lenses normally. These participants were tested without their glasses. There were 30 participants were tested that had normal eyesight and did not wear glasses.

Experiment 4: Children's Clinical Trial:

Subjects: Children aged between 3-7 years were recruited from four clinical sites (Auckland University, Auckland, New Zealand, Texas, USA, and Melbourne, Australia).

Stimuli: Moving stimuli was presented on a 27 inch DELL S2716DG LED monitor, placed 1.5 meters away from children to elicit OKN. The stimuli were patterned disk shaped circles, consisting of a bright inner circle and a darker outer ring. Other controlled parameters included disk size, space, and moving speed. The tables below explain the characteristics of each stimulus at each age group:

3-4 Year Old

| # Syntax: | Note (displayed to operator) | Central intensity (inner contrast) | Perimeter intensity (outter contrast) | Field spacing (degree) | Stroke width (logMar) | Speed (degree/ sec) | Disk type (outter/ inner) | Direction (come from) | Ramp duration (acceleration duration/ seconds) |
|---|---|---|---|---|---|---|---|---|---|
| Disk | Disk presentation 1 | 0.9 | 0.45 | 0.7 | 0.4 | 7 | Disk_2:1 | Left | 2 |
| Disk | Disk presentation 2 | 0.9 | 0.45 | 0.7 | 0.4 | 7 | Disk_2:1 | Right | 2 |
| Disk | Disk presentation 3 | 0.9 | 0.45 | 0.7 | 0.4 | 7 | Disk_2:1 | Left | 2 |
| Disk | Disk presentation 4 | 0.9 | 0.45 | 0.7 | 0.4 | 7 | Disk_2:1 | Right | 2 |
| Disk | Disk presentation 5 | 0.75 | 0.45 | 0.7 | 0.7 | 7 | Disk_2:1 | Left | 2 |
| Disk | Disk presentation 6 | 0.75 | 0.45 | 0.7 | 0.7 | 7 | Disk_2:1 | Right | 2 |

4-5 Year Old

| # Syntax: | Note (displayed to operator) | Central intensity (inner contrast) | Perimeter intensity (outter contrast) | Field spacing (degree) | Stroke width (logMar) | Speed (degree/ sec) | Disk type (outter/ inner) | Direction (come from) | Ramp duration (acceleration duration/ seconds) |
|---|---|---|---|---|---|---|---|---|---|
| Disk | Disk presentation 1 | 0.9 | 0.45 | 0.7 | 0.3 | 7 | Disk_2:1 | Left | 2 |
| Disk | Disk presentation 2 | 0.9 | 0.45 | 0.7 | 0.3 | 7 | Disk_2:1 | Right | 2 |
| Disk | Disk presentation 3 | 0.9 | 0.45 | 0.7 | 0.3 | 7 | Disk_2:1 | Left | 2 |
| Disk | Disk presentation 4 | 0.9 | 0.45 | 0.7 | 0.3 | 7 | Disk_2:1 | Right | 2 |
| Disk | Disk presentation 5 | 0.75 | 0.45 | 0.7 | 0.7 | 7 | Disk_2:1 | Left | 2 |
| Disk | Disk presentation 6 | 0.75 | 0.45 | 0.7 | 0.7 | 7 | Disk_2:1 | Right | 2 |

5-7 Year Old

| # Syntax: | Note (displayed to operator) | Central intensity (inner contrast) | Perimeter intensity (outter contrast) | Field spacing (degree) | Stroke width (logMar) | Speed (degree/ sec) | Disk type (outter/ inner) | Direction (come from) | Ramp duration (acceleration duration/ seconds) |
|---|---|---|---|---|---|---|---|---|---|
| Disk | Disk presentation 1 | 0.9 | 0.45 | 0.7 | 0.2 | 7 | Disk_2:1 | Left | 2 |
| Disk | Disk presentation 2 | 0.9 | 0.45 | 0.7 | 0.2 | 7 | Disk_2:1 | Right | 2 |
| Disk | Disk presentation 3 | 0.9 | 0.45 | 0.7 | 0.2 | 7 | Disk_2:1 | Left | 2 |
| Disk | Disk presentation 4 | 0.9 | 0.45 | 0.7 | 0.2 | 7 | Disk_2:1 | Right | 2 |
| Disk | Disk presentation 5 | 0.75 | 0.45 | 0.7 | 0.7 | 7 | Disk_2:1 | Left | 2 |
| Disk | Disk presentation 6 | 0.75 | 0.45 | 0.7 | 0.7 | 7 | Disk_2:1 | Right | 2 |

Chart-based visual acuity was assessed using a clinical-trial-standard electronic visual acuity system displaying H, O, T and V optotypes. Optotypes were presented individually with crowding bars at 3 meters and optotype size was controlled by a staircase algorithm (see Moke P S, Turpin A H, Beck R W, et al. Computeried method of visual acuity testing: Adaptation of the amblyopia treatment study visual acuity testing protocol. Am J Ophthalmol. 2001; 132:903-9). Test Procedure: Each eye observed four age-specific OKN stimulus presentations/trials that tested the cut-off log MAR visual acuity for referral from a vision screening provided by the American Association for Pediatric Ophthalmology and Strabismus (3-4 year-olds observe 0.4 log MAR; 4-5 years, 0.3 log MAR; and 5-7 years, 0.2 log MAR) and two 0.7 log MAR trials. Each trial lasted 7 seconds, with a 2-second acceleration and 5-seconds of uniform motion. For better attention, stimuli were integrated into an animation of the child's selection. The practitioner triggered presentation of each stimulus when they judged that the child was looking at the screen. The duration between two consecutive trials was 4-10 seconds. Participants were allocated alternately to a HOTV-first stream or an OKN-first stream. For the HOTV-first stream, the right eye was tested first, while for the OKN-first stream, the left eye was tested first.

Data Analysis: Eye movements were recorded using an IDS UI-3140CP infrared camera with a resolution of 1280×1024 pixels. Each video was first analysed objectively using eye tracking software, producing an objective velocity/displacement signal. Then a trained observer watched the videos offline and subjectively graded each. The combination of objective and subjective analysis enabled each trial to be designated OKN present or OKN absent. If any age-specific OKN trials generated an OKN present result, the child passed the screening. If not, they failed. For the HOW test, children passed if they reached the age specific visual acuity cut off and failed if they did not. The sensitivity and specificity of each test were calculated with reference to a gold-standard paediatric eye examination conducted by a qualified clinician which identified whether the child had a vision problem or not.

Results:

23 participants (46 eyes) were analysed. The OKN Visual Acuity System had a specificity and sensitivity for detecting a vision problem of 83.33% and 62.5%. This compared favourably to the HOW test which had a specificity of 100% and a sensitivity of 31.25%. These results indicate that the OKN Visual Acuity System performs as well as, or better than, the current gold standard HOW test for vision problem screening in preschool and school-age children.

The invention claimed is:

1. A method for stimulus and eye tracking useful for the determination of the presence or strength of optokinetic nystagmus (OKN), the method comprising: providing a visual stimulus effective to elicit OKN in front of the eye(s) of a subject by: displaying against a background on a display and varying in visibility, as perceived by the subject, at least one visual stimulus element moving across the display, or displaying against a background a series of at least one visual stimulus element moving across the display so that a later displayed element moving across the display has different visibility, as perceived by the subject, relative to an earner displayed element moving across the display, wherein the moving visual stimulus element or elements comprising a centre and a contrasting perimeter, the perimeter darker than the background and the centre lighter than the background and/or the perimeter lighter than the background and the centre darker than the background, recording video of the subject's eye(s) viewing the stimulus, and image processing the video to detect for OKN.

2. The method according to claim 1 wherein varying the visibility of the visual stimulus element(s) comprises causing the visual stimulus element(s) to vanish or appear (as perceived by the subject).

3. The method according to claim 1 wherein varying the visibility of the visual stimulus element(s) or causing the visual stimulus element(s) to vanish or appear comprises reducing or increasing intensity, contrast, size and/or width of the visual stimulus element(s) or visual stimulus element boundaries.

4. The method according to claim 1 wherein the visual stimulus element or elements comprise:
a perimeter having a perimeter boundary that is darker than a background and a centre having a centre boundary that is lighter than the background, and/or
a perimeter having a perimeter boundary that is lighter than a background and a centre having a centre boundary that is darker than the background.

5. The method according to claim 4 wherein the perimeter has an outer diameter or transverse dimension $OD=\alpha SW$ and thickness $SW(\alpha-1)/2$ where wherein SW is a diameter or transverse dimension of the centre and $\alpha$ is in the range 1 to 5.

6. The method according to claim 4 wherein varying the visibility of the visual stimulus element(s) comprises reducing or increasing an intensity, contrast, or a size and/or width, of the perimeter relative to the centre of the visual stimulus element(s) or of the perimeter relative to a background.

7. The method according to claim 1 wherein a spatial content, speed, temporal frequency, chromatic properties, disparity, and rotation or rotational speed of the stimulus (if not rotationally symmetric) of the visual stimulus varies.

8. The method according to claim 1 wherein the visual stimulus element(s) move across the display with varying visibility as they move across the display.

9. The method according to claim 1 wherein a later displayed element moving across the display has lower or higher visibility relative to an earlier displayed element moving across the display.

10. The method according to claim 1 wherein the perimeter of the visual stimulus element or elements is darker than the background and the centre, an intensity of the centre of the visual stimulus element or elements is between 0.5 to 1.0 of a maximum intensity, and an intensity of the perimeter of the visual stimulus element or elements is between 0 to 0.5 of a maximum intensity.

11. The method according to claim 1 wherein the visual stimulus element(s) comprise circle(s) and/or ellipse(s) and/or disk(s).

12. The method according to claim 11 wherein the method comprises displaying the visual stimulus elements as a single row or column, or in two or more rows and/or two or more columns, or in an array, or as a field of disks.

13. The method according to claim 1 wherein the method comprises displaying multiple visual stimulus elements comprising multiple circles and/or ellipses and/or disks moving across the display.

14. The method according to claim 13 wherein the method comprises displaying the multiple visual stimulus elements moving across the display in series from left to right, or vice versa, in a single row or column, or in two or more rows and/or two or more columns, or in an array, or as a field of disks.

15. The method according to claim 1 wherein the visual stimulus element(s) comprise a center or central disk that is surrounded by a perimeter or annulus or outer disk.

16. The method according to claim 1 wherein the visual stimulus element(s) are in the form of patterned disk-shaped circles comprising a bright inner circle and a darker outer ring, or vice versa.

17. An eye tracking system which comprises: a display arranged to display against a background: at least one visual stimulus element, and vary the visibility thereof, as perceived by the subject, or a series of at least one visual stimulus elements so that a later displayed element has different visibility, as perceived by the subject, relative to an earlier displayed element, wherein the visual stimulus element or elements comprising a centre and a contrasting perimeter, the perimeter darker than the background and the centre lighter than the background and/or the perimeter lighter than the background and the centre darker than the background, a camera arranged to record video of the subject's eye(s) viewing the stimulus, and an image processing system arranged to image process the video to detect the presence or strength of OKN.

18. The system according to claim 17 arranged to vary the visibility of the visual stimulus element(s) by causing the visual stimulus element(s) to vanish or appear (as perceived by the subject).

19. The system according to claim 17 arranged vary the visibility of the visual stimulus element(s) or cause the visual stimulus element(s) to vanish or appear by reducing or increasing intensity, contrast, size and/or width of the visual stimulus element(s) or visual stimulus element boundaries.

20. The system according to claim 17 wherein the visual stimulus element or elements comprise:
a perimeter having a perimeter boundary that is darker than a background and a centre having a centre boundary that is lighter than the background, and/or
a perimeter having a perimeter boundary that is lighter than a background and a centre having a centre boundary that is darker than the background.

21. The system according to claim 20 wherein the perimeter has an outer diameter or transverse dimension $OD=\alpha SW$ and thickness $SW(\alpha-1)/2$ where wherein SW is a diameter or transverse dimension of the centre and $\alpha$ is in the range 1 to 5.

22. The system according to claim 17 arranged to vary the visibility of the visual stimulus element(s) by reducing or increasing an intensity, contrast, or a size and/or width, of the perimeter relative to the centre of the visual stimulus element(s) or of the perimeter relative to a background.

23. The system according to claim 17 arranged to vary a spatial content, speed, temporal frequency, chromatic properties, disparity, and rotation or rotational speed of the stimulus of the visual stimulus.

24. The system according to claim 17 arranged to move the visual stimulus element(s) across the display with varying visibility as they move across the display.

25. The system according to claim 17 arranged to move a later displayed element moving across the display with lower or higher visibility relative to an earlier displayed element moved across the display.

26. The system according to claim 17 wherein the visual stimulus element or elements comprise a perimeter that is darker than a background and a centre, an intensity of the centre of the visual stimulus element or elements is between 0.5 to 1.0 of a maximum intensity, an intensity of the perimeter of the visual stimulus element or elements is between 0 to 0.5 of a maximum intensity.

27. The system according to claim 17 wherein the visual stimulus element(s) comprise circle(s) and/or ellipse(s) and/or disk(s).

28. The system according to claim 27 arranged to display the visual stimulus elements as a single row or column, or in two or more rows and/or two or more columns, or in an array, or as a field of disks.

29. The system according to claim 17 arranged to display multiple visual stimulus elements comprising multiple circles and/or ellipses and/or disks moving across the display.

30. The system according to claim 29 arranged to display the multiple visual stimulus elements moving across the display in series from left to right, or vice versa, in a single row or column, or in two or more rows and/or two or more columns, or in an array, or as a field of disks.

31. The system according to claim 17 wherein the visual stimulus element(s) comprise a center or central disk that is surrounded by a perimeter or annulus or outer disk.

32. The system according to claim 17 wherein the visual stimulus element(s) are in the form of patterned disk-shaped circles comprising a bright inner circle and a darker outer ring, or vice versa.

* * * * *